United States Patent [19]

Rice et al.

[11] Patent Number: 4,762,846

[45] Date of Patent: Aug. 9, 1988

[54] METAPHIT AND RELATED COMPOUNDS AS ACYLATING AGENTS FOR THE (3H)PHENCYCLIDINE RECEPTORS

[75] Inventors: Kenner C. Rice, Rockville, Md.; Michael F. Rafferty, Ann Arbor, Mich.; Arthur E. Jacobson, Potomac, Md.; Patricia Contreras, Bethesda, Md.; Thomas L. O'Donohue, Silver Spring, Md.; Ralph A. Lessor, Bethesda, Md.; Mariena V. Mattson, Wheaton, Md.

[73] Assignee: The United States of America as represented by the Department of Health and Human Services, Washington, D.C.

[21] Appl. No.: 824,848

[22] Filed: Jan. 31, 1986

Related U.S. Application Data

[63] Continuation-in-part of Ser. No. 683,428, Dec. 19, 1984, Pat. No. 4,598,153.

[51] Int. Cl.$^4$ .................. C07D 211/28; A61K 31/26; A61K 31/445
[52] U.S. Cl. ..................................... 514/331; 558/17; 546/229; 514/514
[58] Field of Search ................ 546/229; 514/331, 514; 558/17

[56] References Cited

U.S. PATENT DOCUMENTS 3,097,136  6/1963  Godefroi et al. .................. 546/192
4,196,185  4/1980  Focella et al. ..................... 514/317

OTHER PUBLICATIONS

Quirion et al, Evidence for an Endogenous Peptide Ligand for PCP Recepter, Peptides vol. 5, pp. 967-973 (1984).
Itzhak et al, (I), New Analgesic Drugs Derived from PCP J. Med. Chem 24, pp. 496-499 (1981).
Itzhak et al, II, Receptor Binding and Antinociceptive Prop. of PCP Opiate-Like Derivatives, European J. Pharmacology, 72, pp. 305-311, (1981).
CA 95:24749p, Johnson et al, Synthesis of Amine Derivatives of PCP (1981).

Primary Examiner—Glennon H. Hollrah
Assistant Examiner—D. L. Dinner
Attorney, Agent, or Firm—John S. Roberts, Jr.

[57] ABSTRACT

A derivative of phencyclidine (1) bearing an isothiocyanate moiety on the meta position of the aromatic ring (3; Metaphit as methanesulfonate and HCl salt) has been synthesized and identified as a rapid and specific site-directed acylating agent of the [$^3$H]-phencyclidine binding site in rat brain homogenates. Additional related compounds to Metaphit are Thiophit (oxalate salt), Ethylphit (HCl salt), and Isopropylphit (HCl salt).

1 Claim, 3 Drawing Sheets

METAPHIT AND RELATED COMPOUNDS AS ACYLATING AGENTS FOR THE (3H)PHENCYCLIDINE RECEPTORS

This application is a continuation in part of pending Ser. No. 683,428 filed Dec. 19, 1984, now U.S. Pat. No. 4,598,153, issued July 1, 1986.

Phencyclidine (1-(1-phenylcyclohexyl)piperidine, PCP) is a major drug of abuse due in part to its ability to alter perception in a bizarre manner. PCP also produces violently aggressive behavior and a psychosis that resembles schizophrenia. At least some of the behavioral effects of PCP are thought to be mediated by PCP receptors. Since there is no PCP receptor antagonist, the relevance of PCP receptors has generally been studied by comparing the ability of PCP analogs to induce PCP-like effects to their ability to bind to PCP receptors. Recently Rafferety, et al, *Federation of European Biochemical Societies*, 181:318–322 (1985), synthesized Metaphit (1-(1-(3-isothiocyanatophenyl)cyclohexyl)piperidine), an analog of PCP, that specifically acylates PCP receptors and not opioid, muscarinic, or benzodiazepine receptors.

Metaphit is 1-[1-(3-isothiocyanatophenyl)cyclohexyl]piperidine:

The Metaphit compounds which are similar in action are:

Thiophit

Ethylphit

Isopropylphit

The melting points of these compounds are listed below for the particular salt characterized:

Metaphit, identified as the methanesulfonate salt having a melting point of 175°–176° C.

Thiophit, identified as the oxalate salt having a melting point of 140°–141° C.

Ethylphit, identified as the HCl salt having a melting point of 283°–285° C. and as the amine oxalate salt with a melting point of 170° C.

Isopropylphit, identified as the hydrochloride salt with a melting point of 223°–224° C.

To determine whether Metaphit could produce a long-term antagonism of the behavioral effects of PCP by acylating PCP receptors in vivo, male Sprague-Dawley rats weighing 200–250 g (Taconic Farms, Germantown, N.Y.) were used in experiments. The effect of Metaphit was determined in rats pretreated with Metaphit administered by intracerebroventricular injection (i.c.v.) 24 hours prior to measuring the actions of PCP in binding and behavioral assays. The drugs administered by i.c.v. injection were dissolved in saline such that 5 ul/rat was administered. In the PCP receptor assay, the binding of 2–2000 nM of ($^3$H)PCP (49.9 Ci/mmol, New England Nuclear) to rat brain homogenates prepared from Metaphit- and saline-pretreated rats was determined. At least three binding experiments, each prepared in triplicate, were performed for each drug treatment. The results were analyzed by least squares analysis and reported as mean ±S.E. The behavioral effects of PCP were measured using the PCP rating scale for stereotyped behavior and ataxia. At least 21 rats were used to determine each dose-response curve using behavioral ratings determined 5 minutes after i.c.v. administration of PCP to Metaphit- pretreated rats or to control animals. Dose-response curves were analyzed using a computerized Finney assay.

The binding of ($^3$H)PCP determined in Metaphit- and saline-pretreated rats by the i.c.v. route indicated that there was a 25% and 40% decrease in the $B_{max}$ of ($^3$H)PCP determined in rats pretreated with 1 umol/rat ($B_{max}$ =1550±70 fmol/mg) and 2 umol/rat ($B_{max}$=1230±110 fmol/mg) of Metaphit, respectively. However, there was no significant difference between the $K_D$ values for ($^3$H)PCP determined in rats pretreated with saline (KD=237±8 nM), or with Metaphit at a concentration of 1 umol/rat ($K_D$=237±8 nM) or 2 umol/rat ($K_D$=219±24 nM). Since the preparation of the brain homogenates included two washings and was prepared 24 hours after Metaphit was administered, these results support the findings of Rafferty, et al, supra, that Metaphit binds irreversibly to PCP receptors.

The ability of PCP to induce stereotyped behavior and ataxia in control and Metaphit-pretreated rats was measured to determine whether acylation of PCP receptors would antagonize the behavioral effects of PCP. At an i.c.v. dose of 1 umol/rat, Metaphit produced a 3- and 2-fold shift to the right in the dose-response curves for stereotyped behavior and ataxia, respectively. At a larger dose of 2 umol/rat, Metaphit shifted the dose-response curves for stereotyped behavior and ataxia 7- and 5-fold to the right, respectively. Thus, 24 hours after Metaphit was administered i.c.v., Metaphit produced a dose-dependent antagonism of the ability of PCP to induce stereotyped behavior and ataxia.

This antagonism of PCP's behavioral effects was not due to a non-selective depressant effect as Metaphit did not antagonize amphetamine-induced stereotypy. Also, the effects of Metaphit were not due to a neurotoxic effect as the ED50 values for stereotypy and ataxia returned to control values within 5 days. It is also unlikely that antagonism of PCP's behavioral effects by Metaphit is due to acylation of receptors other than PCP receptors because Metaphit has been found not to acylate opioid, muscarinic, or benzodiazepine receptors in vitro (Rafferty, et al, supra). The in vivo results indicate that Metaphit could antagonize the actions of PCP by binding irreversibly to PCP receptors. Thus, Metaphit is the first drug that can be used to antagonize the actions of PCP that are mediated by PCP receptors. Antagonism of PCP-induced stereotyped behavior and ataxia by Metaphit, indicates a role for PCP receptors in mediating these behaviors. Metaphit, which has been previously shown to acylate PCP receptors, antagonized PCP-induced stereotyped behavior and ataxia by reducing the number of available PCP receptors.

Evidence has been obtained for the presence of specific receptors in the brain for PCP and PCP-like compounds. Binding sites for which PCP-like compounds have high affinity have been noted to be most prevalent in the striatum, cortex, and hippocampal regions of the brain. There is a high statistical correlation between the binding affinity of these compounds in vitro and their in vivo activity. The stereospecificity of the interaction of PCP-like compounds with the PCP receptors in vitro and in vivo has also been noted. Further, an endogeneous ligand for the PCP receptor is known. There is also previous evidence that multiple receptors may exist for PCP-like compounds. The effect of Metaphit on the binding of PCP in striatum has been correlated with a diminished behavioral efficacy of PCP.

Stereospecific PCP-induced depressions of cerebellar Purkinje neurons are mediated by catecholamine pathways. The stereospecific effect of the PCP derivative, 1-(1-phenylcyclohexyl)-3-methyl-piperidine (PCMP), on cerebellar Purkinje neurons is blocked by antipsychotics in a dose-dependent manner, analogous to the blockade of similar NE effects in this brain region. This antagonism is pharmacologically specific since no antagonism of GABA-induced inhibitions by neuroleptic drugs was seen. In addition, the local administration of lithium, which has been shown to block NE effects on cerebellar Purkinje neurons, also strongly antagonized PCP-induced depressions. These noradrenomimetic effects of PCP may be mediated presynaptically in the cerebellum, since local disruption of transmitter release with iontophoretically applied $Mg^{++}$ results in decreased PCP efficacy. Also, selective destruction of cerebellar NE-containing afferents with 6-OHDA completely eliminates stereospecific Purkinje cell responses to PCMP.

The compound Ketamine is a dissociative anesthetic used clinically which produces schizophreniclike and other psychotic states. Thus, the psychiatric use of Metaphit may be projected beyond PCP and Ketamine. The structure for Ketamine is as follows:

Ketamine, an analog of PCP, is also a dissociative anesthetic. Ketamine produces anesthesia with psychotomimetic effects that do not occur as frequently as with PCP. Ketamine is currently used as an anesthetic in the practice of medicine for certain situations such as burn cases and in small children and pregnant women. Ketamine has some effects in common with phencyclidine as a dissociative anesthetic and Metaphit may be useful as an antagonist for side-effects produced during Ketamine anesthesia. Some side effects of Ketamine anesthesia are similar to those of phencyclidine abuse. A functional antagonist for Ketamine would eliminate the side effects produced after Ketamine anesthesia. One further factor is that phencyclidine exerts its effects in the central nervous system by acting on receptor sites (analogous to the opiates) and Metaphit is a valuable research tool for this circuitry in the brain and greatly facilitates study of the structure and function of the phencyclidine recognition site in the central nervous system.

Material Information Disclosure

The following patents are of interest: U.S. Pat. No. 3,097,136 Godefroi et al, phencyclidine, and U.S. Pat. No. 4,196,185 Focella et al. Relative to No. 4,196,185, this patent deals with development of an immunoassay for phencyclidine. Focella et al prepare a carboxylic acid derivative of phencyclidine and use this compound as a ligand to couple to bovine serum albumin. This drug, coupled with protein, can be used to generate antibodies against the phencyclidine derivatives. The phencyclidine derivative is a carboxylic acid and it is coupled in the standard way to bovine serum albumin using carbodiimide methodology. The coupling of this compound through an amide system is standard technique. A benzoic acid derivative which is used as the haptan will not couple in the absence of the carbodiimide reagent. Metaphit, on the other hand, is a site directed acylating agent for phencyclidine receptors. The electrophilic function is already built into Metaphit as an isothiocyanate function. The inherent affinity of the phencyclidine carbon nitrogen skeleton causes binding to the receptor and then the electrophilic function already present in Metaphit, the isothiocyanate function, forms a covalent bond with the receptors. Metaphit is a specific acylating agent for phencyclidine receptors to the exclusion of benzodiazepine receptors, opiate receptors, and QNB receptors.

The illicit use of phencyclidine (PCP) is a major problem in the United States that has rivaled the abuse of heroin and cocaine. The bizarre dissociative behavioral effects produced in humans by PCP range from schizophrenia-like states to violently aggressive behavior and self-mutilation. These effects have stimulated interest in the biochemical pharmacology of PCP and recent studies have described stereoselective, saturable binding sites in rat brain and other species. Despite some initial controversy concerning the pharmacological relevance of the site, a high degree of correlation between binding affinity and in vivo activity of several PCP-mimetics support the contention that the site is indeed a pharmacological receptor. The recent finding of an endogenous peptide with a binding affinity much greater than PCP for this site raises questions concerning the physiological function of these sites in the CNS and their involvement in neuropsychiatric states.

Recent efforts of the present inventors have resulted in the synthesis of compounds which specifically acylate mu and delta opioid receptor subtypes. In view of the relation between the [$^3$H]PCP binding site and the putative sigma opiate receptor, there have been synthesized PCP derivatives bearing acylating and alkylating functional groups in an attempt to develop an affinity label for this recognition site which could prove to be of value in probing its role in the CNS and aid in isolation and characterization of the binding site proteins. The present invention is a synthesis and biochemical characterization of the first electrophilic acylating PCP derivative 1-[1-(3-isothiocyanatophenyl)cyclohexyl]piperidine, which is termed "Metaphit."

1. X = H(PCP)
2. X = NCS (METAPHIT)

Metaphit was prepared from the known PCP analogue where X=NH$_2$ using standard procedures and was fully characterized by spectral data and combustion analysis.

The acylating specificity of Metaphit for the [$^3$H]PCP site was determined because PCP and its congeners have been reported to interact at cholingergic receptors and with opioid receptors and possess analgesic activity. Metaphit was found to displace [$^3$H]QNB (quinuclidinyl benzilate) from muscarinic receptors in rat brain homogenates with a potency equivalent to PCP, without a significant loss of QNB binding compared with control tissues (Table 1). Likewise, Metaphit competitively inhibited [$^3$H]dihydromorphine binding but no irreversible blockade of opioid receptors could be observed. Metaphit was inactive in all respects toward the [3H]diazepam site. These data indicate that Metaphit is highly specific as a covalent labelling reagent.

In summary, the PCP congener Metaphit has been found to covalently modify a significant portion of the [$^3$H]PCP binding sites found in rat brain.

In Table 1 below, which shows the ability of Metaphit to reversibly and irreversibly antagonize binding of various brain receptor ligands, the ligand concentrations used were 8 nM [$^3$H]phencyclidine, 0.5 nM [$^3$H]QNB, 1 nM [$^3$H]dihydromorphine, and 5 nM [$^3$H]diazepam. The binding methodology for PCP was modified, the others were from known methods; i.e., Yamamura et al, *Proc. Nat. Acad. Sci. U.S.A.*, 71:1725 (1974); Paul et al, *Science*, 202:892 (1978); Gabrielevitz et al, *Life Sci.*, 26:89 (1980); and Itzhak et al, *Eur. J. Pharmacol.*, 72:305 (1981). Specific binding refers to the per cent binding remaining in washed, treated tissue compared with similarly washed controls. IC50 values for Metaphit were estimated from competitive displacement curves.

TABLE 1

| Ability of Metaphit to Reversibly and Irreversibly Antagonize Binding of Various Brain Receptor Ligands | | | |
|---|---|---|---|
| Ligand | Maximum % Alkylation by 10 uM Metaphit | IC$_{50}$, uM for Metaphit | IC$_{50}$, uM for PCP |
| [$^3$H]PCP | | | |
| Hippocampus | 45* | — | 0.075 |
| Striatum | 50* | — | 0.070 |
| [$^3$H]QNB | 0 | 19 | 25 |
| [$^3$H]Dihydromorphine | 0 | 11 | 13** |
| [$^3$H]Diazepam | 0 | >1000 | >200 |

*These average numbers are not statistically different
**Obtained from Itzhak et al, Eur. J. Pharmacol., 72:305 (1981)

Metaphit, 1-(1-(3-isothiocyanatophenyl)cyclohexyl)-piperidine, produced a dose-dependent decrease in the number of PCP receptors determined in brain homogenates from rats pretreated with Metaphit 24 hours before sacrifice as compared to control values. The same doses of Metaphit that decreased PCP binding also antagonized PCP-induced sterotypy and ataxia. This antagonism was evident 1 and 24 hours after Metaphit pretreatment and was dose-dependent. These results suggest that irreversible binding of Metaphit to PCP receptors antagonized PCP-induced sterotypy and ataxia. Thus, Metaphit is the first drug that directly antagonizes the behavioral effects of PCP by inhibiting the interaction with PCP receptors.

Phencyclidine (1-(1-phenylcyclohexyl)piperidine, angel dust, PCP) was first synthesized as a general anesthetic by the Parke Davis Pharmaceutical Company. However, its use as an anesthetic was soon terminated because of psychological side effects, which could last more than 12 hours. PCP is currently a major drug of abuse due in part to its ability to produce euphoria, excitation and to alter perception in a bizarre manner. In addition, PCP can also produce violently aggressive behavior and a persistent psychosis. The PCP-induced psychosis is often referred to as schizophrenia-like because of the similarities between the symptoms of acute schizophrenia and the PCP psychosis. Indeed, it has even been suggested that the use of PCP instead of amphetamines would provide a better drug model for schizophrenia. Since the mechanism of action of PCP is not known, there is still no specific treatment for PCP intoxication and psychosis.

At least some of the pharmacological effects of PCP are thought to be mediated by PCP receptors. PCP receptors have a unique distribution, with highest concentrations in the hippocampus and cortex and high concentrations in the nucleus accumbens, all of which may be relevant to PCP's psychotomimetic properties. Also, the pharmacological relevance of PCP receptors is supported by reports that the ability of PCP analogs to generalize to PCP stimulus, induce sterotypy, and alter 2-deoxyglucose metabolism correlates well with their ability to bind to PCP receptors. However, there are conflicting reports on the correlation between the structural requirements for induction of ataxia and PCP receptor binding. Unfortunately, until now there has not been a selective PCP receptor antagonist available to determine whether binding to PCP receptors is necessary for pharmacological activity. A PCP receptor antagonist would not only be useful in evaluating which effects of PCP are mediated by PCP receptors but could also potentially be applied to the treatment of PCP intoxication or the psychotomimetic side effects of ketamine, a PCP-like anesthetic. The purpose of the present invention is to disclose the in vivo effects of Metaphit, a PCP analog that has been shown to acylate PCP receptors using in vitro binding assays.

DESCRIPTION OF THE FIGURES

FIG. 1 shows examples of Scatchard plots of 3H-PCP binding in a crude membrane preparation from rats pretreated with saline (●), 1 umol/rat ( 0 ) or 2 umol/rat (□) of Metaphit. A crude membrane preparation in 5 mM Tris-HCl, pH 7.4 (Tris buffer) was prepared from the brains of rats pretreated with saline or Metaphit administered i.c.v. 24 hours before sacrifice. Incubation tubes, prepared in triplicate, contained a varying amount of 3H-PCP (New England Nuclear) made up in Tris buffer, 100 $\mu$l of membrane preparation and enough Tris buffer to make a total volume of 500 $\mu$l. The tubes were incubated for 50 minutes on ice and filtered through Whatman GF/B filters, which were presoaked for at least 2 hours in 0.05% polyethylenimine. The test tubes were washed twice and the filters once more with 4 ml of ice-cold Tris buffer. The filters were placed into scintillation vials containing 10 ml of Aquassure and radioactivity counted by liquid scintillation spectrometry. Protein concentrations were determined by the method of Lowry et al, *J. Biol. Chem.*, 193:254 (1951).

Synthesis of Metaphit

Metaphit was prepared as methanesulfonate and hydrochloride salts. To a vigorously stirred two-phase system consisting of 4.65 g (18 mmol) of m-amino-PCP (1-(1-(3-aminophenyl)cyclohexyl)piperidine) in 50 ml of chloroform and 756 mg (90 mmol) of sodium bicarbonate in 25 ml water, was added a solution of 1.45 ml (2.29 g, 19 mmol) of freshly distilled thiophosgene in 10 ml of chloroform. The mixture was stirred for 5 minutes, then the phases were separated and the aqueous phase was washed once with chloroform. The combined organic layers were dried (over sodium sulfate) and evaporated to a clear glass (5.43 g). This substance was dissolved in tetrahydrofuran (20 ml) and treated with a solution of methanesulfonic acid (1.73 g, 18 mmol) in tetrahydrofuran. The resulting crystalline solid was filtered and dried in vacuo to give 7.01 g (98%) of methanesulfonate salt, mp 175°–178° C. (dec). The material could be recrystallized from isopropanol/isopropyl ether if necessary. It was stored at 0° C. in a dessicator. The hydrochloride salt prepared in isopropanol and recrystallized from methanol-ether showed mp 214°–216 ° C. The methanesulfonate salt was considerably more soluble in water than the hydrochloride.

Biochemical Procedure

The present in vitro assay procedure is adapted from Zukin et al., *Brain Res.*, 258:277–284, 1983, and uses adult male Sprague-Dawley rats (Taconic Farms, Germantown, N.Y.). It has been described previously (Rafferty et al., supra, 1985), using 8 nM [3H]-PCP as the radioligand, and homogenates from rat striatum and/or hippocampus. The assay of the present invention now utilizes 5 nM [3H]-TCP (New England Nuclear, 55.3 Ci/mmol). The displacement assays are carried out using whole rat brain homogenate (minus cerebellum and brain stem). Non-specific binding is estimated using 10 uM unlabelled TCP.

[3H]-TCP, rather than [3H]-PCP, is preferable as the radioligand in the PCP assay. TCP has considerably higher affinity for the PCP receptor than PCP. Non-specific binding decreased from 30% of the total binding with [3H]-PCP to 10% using [3H]-TCP. The decrease in non-specific binding enabled simplification of the tissue preparation and use of brain homogenate (minus the cerebellum and brain stem), rather than striatum and hippocampus.

Starting materials and target compounds were evaluated for their affinity for phencyclidine receptors by displacement assays. The apparent IC50 for PCP and PCE (3a, Scheme 1) were similar (150 nM for PCP and 240 nM for PCE), using 8 nM [3H]-PCP as the radioligand in rat striatum and hippocampus homogenate. PCI (4a, Scheme 2) had an apparent IC50 of 50 nM in that assay, and TCP (5a, Scheme 3) was twice as potent as PCI.

The affinities of the potential affinity ligands are all reduced compared to the parent compounds, but were sufficiently high to warrant their further testing as irreversible ligands. Of the three new compounds (3b, 4b, and 5b, Schemes 1, 2, and 3, respectively), the thienyl compound (5b) displays considerably higher affinity for the PCP receptor (Table 2 below). It should be noted that determination of a true IC50 for these affinity ligands is not possible due to their rapid and irreversible interaction with some of the receptor population under the assay conditions.

TABLE 2

Affinity of Ligands for the Phencyclidine Receptor in Rat Brain Homogenate

| Compound | Apparent IC$_{50}$, nM |
|---|---|
| PCP | 70 |
| Metaphit | 2800 |
| Ethylphit (3b) | 3840 |
| Isopropylphit (4b) | 2700 |
| TCP (5a) | 20 |
| Thiophit (5b) | 900 |

The ability of the potential affinity ligands 3b, 4b, and 5b to interact irreversibly with the phencyclidine receptor was explored at two concentrations. Briefly, the tissue homogenate was incubated with the test drug (10 $\mu$M and 100 $\mu$M concentration) for 10 minutes, then washed several times and evaluated by displacement of tritiated TCP with unlabeled TCP. Under these conditions, 2 $\mu$M TCP or 10 uM PCP, alone, were completely washed out of the homogenate. With the affinity ligands, a significant loss of binding sites was observed. All of the four affinity ligands completely inhibited the PCP receptors at a concentration of 100 $\mu$M.

At 10 $\mu$M, both Metaphit and Thiophit inhibited about 50 to 56% of the receptor population, irreversibly. Isopropylphit and Ethylphit appeared to be more effective, irreversibly interacting with about 62 to 67% of the PCP receptors at the 10 $\mu$M concentration. Thiophit had a much higher affinity for the PCP receptors, in displacement assays, than either of the other two affinity ligands.

The irreversible interaction of thiophit on PCP receptors was further examined to see whether it interacted with the same set of PCP receptors as metaphit. Scatchard analyses were obtained in the presence and absence of 10 μM thiophit and metaphit, using various concentrations of [3H]-TCP (1.0 to 150 nM). The data, analyzed by least squares.linear regression, revealed a significant loss of binding sites in the tissues treated with the affinity ligands, with no significant alteration in the affinity of the remaining sites (Kd for control, 0.015 μM, Kd for metaphit-treated tissue 0.021 μM, Kd for thiophit-treated tissue 0.027 μM; Bmax for control, 1000 fmol/mg protein, Bmax for metaphit- or thiophit-treated tissue 700 fmol/mg protein). Thus, about a 30% reduction was seen in Bmax for either thiophit or metaphit treated homogenate. These data indicated that thiophit and metaphit exerted similar effects, and probably interacted irreversibly with the same population of PCP receptors.

The present invention has synthesized three new electrophilic affinity ligands for the PCP receptor, thiophit (5b), ethylphit (3b), and isopropylphit (4b), each of which are effective irreversible inhibitors. Thiophit has considerably higher affinity for the PCP receptor than either of the other two affinity ligands and is three times as potent as metaphit at the PCP receptor in displacement assays.

In regard to the question of the utility of Metaphit in blocking the action of PCP, experiments of the present invention have shown that Metaphit is effective in antagonizing the action of PCP, whether it is given before or after PCP administration. This is due to the fact that Metaphit will bind to the receptors when it is administered and prevent circulating PCP from binding to the receptors and causing further actions. Therefore, Metaphit could be administered in an emergency room setting to block the actions of PCP or as post-anesthetic medication to block psychotomimetic actions of ketamine.

With respect to whether the rat model is a useful predictor of actions in humans, experiments of the present invention indicate that the rat and human PCP receptors are pharmacologically identical as compounds such as Metaphit that bind to the rat receptor also bind to the human receptor. The next aspect of this question concerns whether the antagonism of stereotypy in rat is an index of the blockade of hallucinations or psychoses in man. The antagonism of stereotypy is the classical screen for anti-psychotic potential.

Metaphit has been administered by all possible parenteral routes. Similar to the results found for i.c.v. administration, the drug was effective at inhibiting the induction of stereotypy by phencyclidine after i.v. administration. The drug was not effective at the doses tested after sc or ip administration. These were not tested at higher doses as the most likely and most desirable route of administration for Metaphit would be the iv route.

With respect to the details of behavioral tests and receptor binding methodology, the Contreras, et al, manuscript, "Metaphit, an Acylating Ligand for Phencyclidine Receptors: Characterization of In Vivo Actions in the Rat," describes this methodology.

Dosage

The dosage of Metaphit or its related compounds noted in this application in relation to phencyclidine or ketamine is generally in the ratio of 1:2 to 2:1 effective weight percent with an optimum value of about 1:1 and the mode is by injection preferably i.v.

EXAMPLE 1

Even though Metaphit has been shown to acylate PCP receptors when added to brain homogenates in vitro, it is still necessary to determine whether Metaphit acylates PCP receptors when administered in vivo. This question was answered by kinetic analysis of 3H-PCP binding in saline and Metaphit-pretreated rats. Male Sprague-Dawley rats (Taconic Farms, Germantown, N.Y.) weighing 200–250 g were used in all experiments. All rats were anesthetized lightly with ether before a 20-gauge needle was used to make a hole in the skull of rats for intracerebroventricular (i.c.v.) injection of drugs. The animals were allowed at least 1 day to recover before being used. The 3H-PCP binding assay was adapted from the method of Quirion et al, *Peptides*, 5:967–973, 1984 (see description of FIG. 1). Specific binding was defined as total radioligand bound minus the amount of radioligand bound in the presence of 30 uM PCP. Kd and Bmax values were determined by least squares regression. The results are expressed as the mean ±S.E. of at least three experiments.

Figure 1:
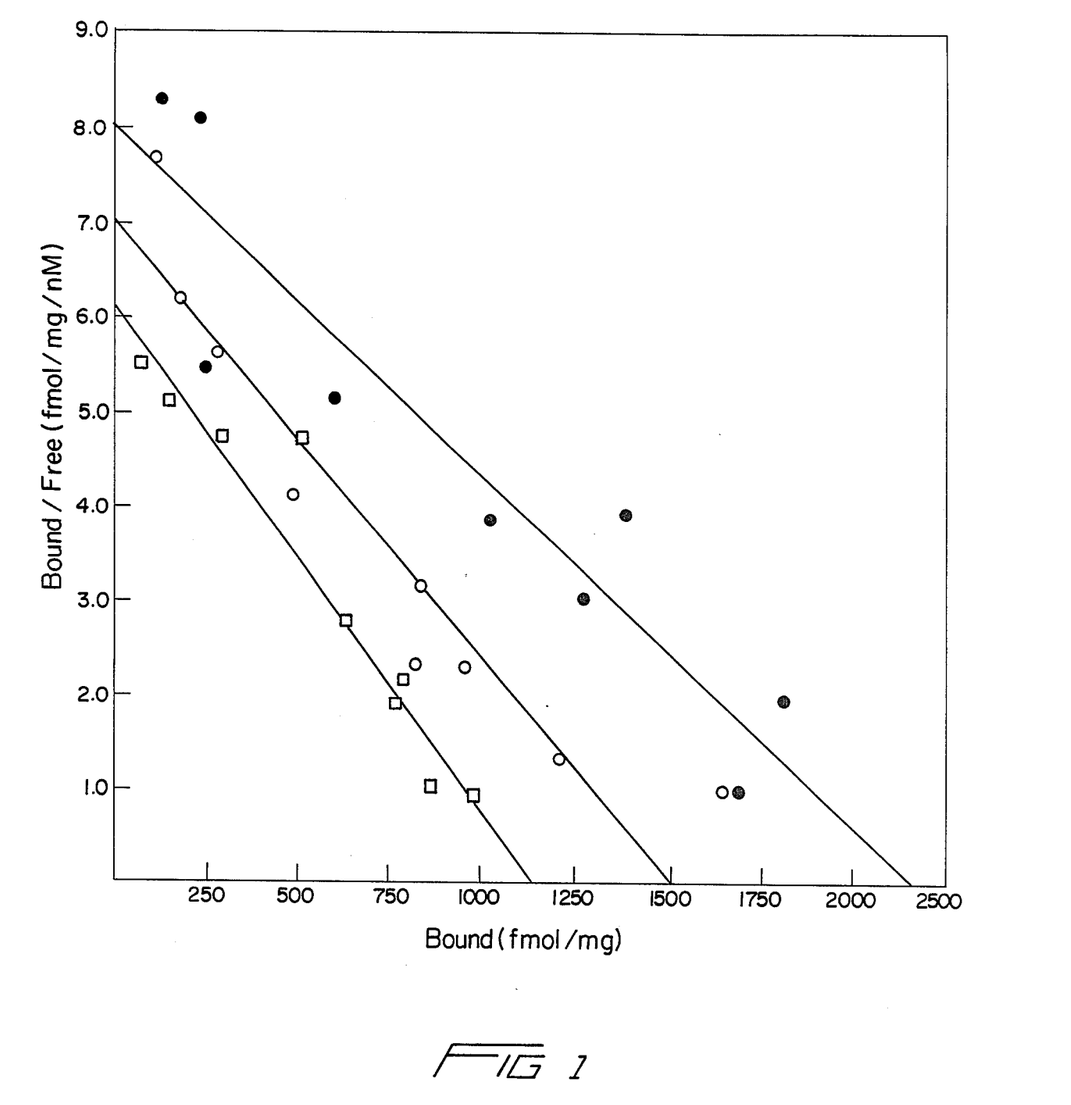

An example of Scatchard plots of 3H-PCP binding in membrane preparations from rats treated with saline or Metaphit 24 hours prior to sacrifice is shown in FIG. 1. There was no significant difference between the Kd values for 3H-PCP determined in rats pretreated with saline (Kd=237±8 nM), 1 μmol/rat (Kd=237±8 nM) or 2 μmol/rat of Metaphit (Kd=219±24 nM). However, there was a 25% and 40% decrease in the Bmax of 3H-PCP determined in rats pretreated with 1 μmol/rat (Bmax=1550±70 fmol/mg) and 2 μmol/rat (Bmax=1230±50 fmol/mg) of Metaphit, respectively, as compared to control (Bmax=2030±110 fmol/mg). These results indicate that Metaphit binds irreversibly to PCP receptors as administration of the drug changed only the number of binding sites without altering the affinity of binding in a dose-dependent manner and this effect was evident 24 hours after Metaphit pretreatment.

EXAMPLE 2

For the behavioral experiments concerning whether acylation of PCP receptors by Metaphit was associated with any changes in PCP's behavioral effects, rats were placed individually into 27×44×18 cm high plastic rat cages and allowed at least 1 hour to acclimate before testing began. PCP or Metaphit was administered by i.c.v. injection in 5 ul of saline. Stereotypy and ataxia were measured at 5 min intervals using a PCP rating scale. A rating of 5 was considered a 100% response. Dose-response curves of PCP represent behavioral ratings determined 5 min after PCP administration, the time of peak effect. At least 21 rats were used to determine each dose-response curve and ED50. ED50 values and dose-response curves were evaluated using the Finney assay (*Statistical Methods in Biological Assay*, 2nd ed., Hafner Publishing Co., N.Y., 1964) with the aid of a computer.

Figure 2:
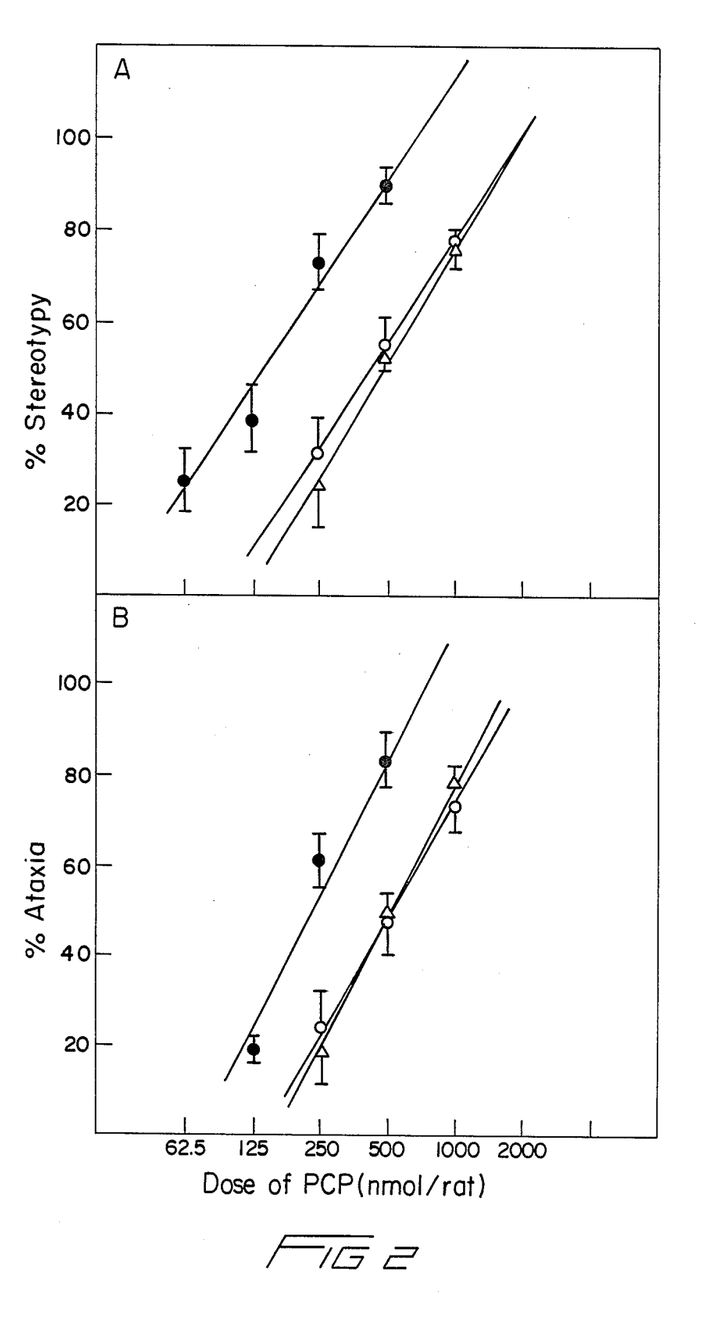
FIG. 2 shows PCP dose-response curves for (a) stereotypy and (b) ataxia determined in control rats (●), or 1 hour (Δ) or 24 hours ( 0 ) after i.c.v administration of 1 $\mu$mol/rat of Metaphit.
Figure 3:
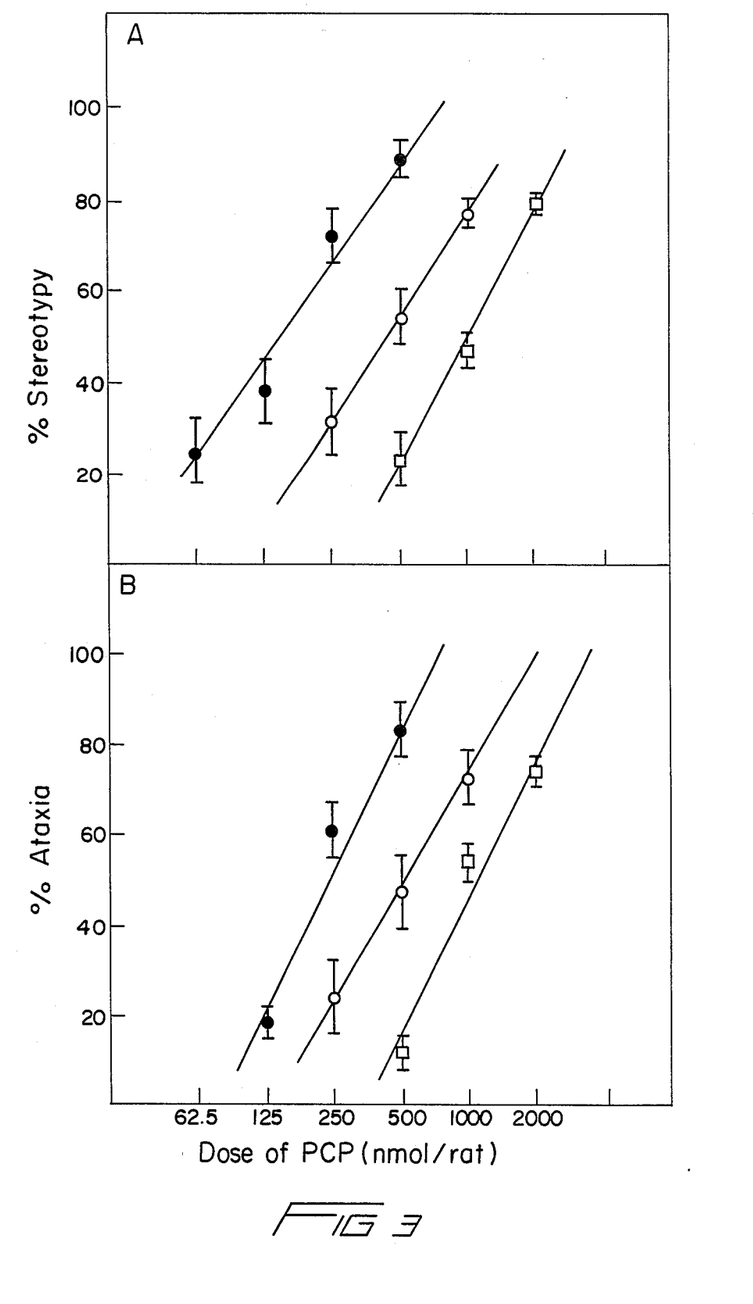
FIG. 3 shows PCP dose-response curves for (a) stereotypy and (b) ataxia determined in control rats (●) or 24 hours after i.c.v. administration of 1 umol/rat ( 0 ) or 2 umol/rat (□) of Metaphit.

Metaphit at a dose of 1 μmol/rat did not produce any significant behavioral effects, but a dose of 2–8 μmol/rat produced what appeared to be a calming effect as the rats generally remained stationary in a resting position in one spot, yet were not ataxic or catatonic and were generally alert. At these higher doses, a few rats exhibited qualitative changes similar to those exhibited by PCP treated rats, which were not quantitatively significant. The ability of PCP to induce stereotypy and ataxia was then evaluated 1 hour after 1 μmol/rat of Metaphit. As illustrated in FIG. 2, PCP dose-response curves for stereotypy and ataxia were shifted significantly 3- and 2-fold, respectively, to the right of the control dose-response curves. This antagonism of PCP by 1 μmol/rat of Metaphit was still evident 24 hours after Metaphit pretreatment, as the PCP dose-response curves for stereotypy and ataxia determined 24 hours after Metaphit pretreatment were not significantly different from those determined 1 hour after Metaphit pretreatment. The antagonism of PCP-induced stereotypy and ataxia was also dose-dependent (FIG. 3). Twenty-four hours after administration of 2 μmol/rat of Metaphit, the PCP dose-response curves for stereotypy and ataxia were shifted 7- and 5-fold, respectively, to the right as compared to control.

EXAMPLE 3

Synthesis of Ethylphit

The synthetic routes to 3b, 4b, and 5b all involve nitration of the aromatic nucleus as the key step in functionalization. Thus, nitration of PCE (3a) afforded meta-nitro PCE (3a) as the major product (Scheme 1). Reduction with hydrogen over palladium afforded the amino compound 3d, which was converted to the isothiocyanate 3b by treatment with thiophosgene in a two-phase system of aqueous sodium bicarbonate and chloroform.

Scheme 1

Nitration of PCE: synthesis of (1-(3-nitrophenyl)cyclohexylethylamine.HCl

(1-Phenylcyclohexyl)ethylamine hydrochloride (6.50 g, 27 mmol) was dissolved in 35 mL of concentrated sulfuric acid which had been pre-cooled to 5° C. The mixture was stirred in an ice-water bath until solution was complete. 2.0 mL of 70% nitric acid was added and the mixture stirred at 0°–5° C. for 1 hour. The reaction was poured onto 150 g of ice and neutralized with concentrated ammonium hydroxide to pH 9. The resulting suspension was extracted four times with 75 mL portions of chloroform. The combined organic layers were dried over anhydrous sodium sulfate, filtered, and evaporated to give a yellow oil. The oil was dissolved in acetone (50 mL) and acidified with a solution of hydrogen chloride gas in isopropanol. The resulting pale yellow crystals were filtered and washed with ethyl ethers, affording 5.6 g (75% yield) of product. The hydrochloride salt could be recrystallized from water/methanol (3:1) to give yellow crystals, which displayed a melting point of 283°–285° C. with gas evolution and browning, with a preliminary phase change at about 265° C.

EXAMPLE 4

Synthesis of Isopropylphit

Nitration of PCI under similar conditions gave an inseparable mixture of meta- and para-nitro isomers 4c and 4d (Scheme 2). Hydrogenation of this mixture gave the meta-amino compound 4e.

The synthesis is as shown below.

Scheme 2

EXAMPLE 5

Synthesis of Thiophit

Nitration of TCP afforded primarily the 5-nitrothienylcyclohexylpiperidine 5c, along with about 15% of the 4-nitro compound 5d (Scheme 3). The complete synthesis is given below:

Scheme 3

Attempts to reduce 5c led to decomposition, presumably involving loss of piperidine via a mechanism similar to that proposed for the decomposition of para-amino PCI. Bromination of TCP in hot glacial acetic acid afforded the 5-bromo TCP (5e). Nitration of this compound afforded a single product, which was assigned structure 5f on the basis of further transformations (vide infra). Catalytic reduction of 5f afforded the air-sensitive 4-amino TCP (5g), which was not isolated but was converted directly to the isothiocyanate 5b as before. Proton NMR studies of this compound confirmed the position of the isothiocyanate group, with the coupling constant between the 3- and 5-protons of the thiophene ring being less than 1 Hertz, while in the parent TCP 5a the observed ortho coupling was about 4 Hertz between H-4 and both H-3 and H-5. All new compounds were fully characterized by C, H, and N combustion analyses, NMR, mass and infrared spectroscopy.

We claim:
1. A compound selected from the group consisting of
   Thiophit, 1-[1-2(1-isothiocyanato)thionyl)cyclohexyl]piperidine, having a melting point as the oxalate salt of 140°–141° C.
   Ethylphit, N[1-m-isothiocyanato-phenyl]cyclohexyl]ethylamine, having a melting point as the HCl salt of 283°–285° C. and as the amine oxalate salt of 170° C. and
   Isopropylphit, N-[1-(m-isothiocyanatophenyl)cyclohexyl]isopropylamine, having melting point as the hydrochloride salt of 223°–224° C.

* * * * *